United States Patent
Wall, III et al.

(10) Patent No.: US 9,389,431 B2
(45) Date of Patent: Jul. 12, 2016

(54) CONTEXTUAL IMAGE STABILIZATION

(71) Applicants: MASSACHUSETTS EYE & EAR INFIRMARY, Boston, MA (US); THE UNITED STATES OF AMERICA AS REPRESENTED BY THE DEPARTMENT OF VETERANS AFFAIRS, Washington, DC (US)

(72) Inventors: Conrad Wall, III, Boston, MA (US); Minnan Xu, Cambridge, MA (US); Joseph F. Rizzo, III, Newton, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 250 days.

(21) Appl. No.: 14/356,065

(22) PCT Filed: Nov. 5, 2012

(86) PCT No.: PCT/US2012/063577
§ 371 (c)(1),
(2) Date: May 2, 2014

(87) PCT Pub. No.: WO2013/067513
PCT Pub. Date: May 10, 2013

(65) Prior Publication Data
US 2014/0303687 A1    Oct. 9, 2014

Related U.S. Application Data

(60) Provisional application No. 61/555,908, filed on Nov. 4, 2011, provisional application No. 61/555,930, filed on Nov. 4, 2011.

(51) Int. Cl.
*H04N 5/232* (2006.01)
*A61N 1/36* (2006.01)
(Continued)

(52) U.S. Cl.
CPC . *G02C 5/001* (2013.01); *A61F 9/08* (2013.01); *A61H 3/061* (2013.01);
(Continued)

(58) Field of Classification Search
CPC .................. H04N 5/23261; H04N 5/23287
See application file for complete search history.

(56) References Cited

U.S. PATENT DOCUMENTS

| 3,383,682 A | 5/1968 | Stephens, Jr |
| 4,992,998 A | 2/1991 | Woodward |

(Continued)

FOREIGN PATENT DOCUMENTS

| CN | 101076841 | 11/2007 |
| CN | 200984304 | 12/2007 |

(Continued)

OTHER PUBLICATIONS

Chinese Office Action in Chinese Application No. 201280066158.8, dated Oct. 8, 2015, 28 pages (with English Translation).

(Continued)

*Primary Examiner* — W B Perkey
(74) *Attorney, Agent, or Firm* — Fish & Richardson P.C.

(57) ABSTRACT

Image stabilization systems and methods include a detector configured to detect images, an actuator coupled to the detector, a sensor coupled to the detector and configured to detect motion of the detector, and an electronic processor in communication with the sensor and the actuator, where the electronic processor is configured to, for example: (a) receive information about motion of the detector from the sensor; (b) determine components of the motion of the detector, and associate a class with each of the determined components; (c) identify components to be compensated from among the determined components based on the associated classes; and (d) generate a control signal that causes the actuator to adjust a position of at least a portion of the detector to compensate for the identified components.

20 Claims, 6 Drawing Sheets

(51) Int. Cl.
*G02C 5/00* (2006.01)
*G02B 27/64* (2006.01)
*A61H 3/06* (2006.01)
*A61F 9/08* (2006.01)
*G02C 11/00* (2006.01)

(52) U.S. Cl.
CPC ......... *A61N 1/36046* (2013.01); *G02B 27/646* (2013.01); *G02C 11/10* (2013.01); *H04N 5/23258* (2013.01); *H04N 5/23267* (2013.01); *H04N 5/23287* (2013.01); *A61H 2201/0184* (2013.01); *A61H 2201/165* (2013.01); *A61H 2201/501* (2013.01); *A61H 2201/503* (2013.01); *A61H 2201/5007* (2013.01); *A61H 2201/5048* (2013.01); *A61H 2201/5069* (2013.01); *A61H 2201/5079* (2013.01); *A61H 2201/5084* (2013.01); *A61H 2201/5092* (2013.01); *A61H 2201/5097* (2013.01); *G03B 2205/0007* (2013.01); *G03B 2217/005* (2013.01); *H04N 5/23261* (2013.01)

(56) References Cited

U.S. PATENT DOCUMENTS

| | | | |
|---|---|---|---|
| 5,159,927 A | 11/1992 | Schmid | |
| 5,411,540 A | 5/1995 | Edell et al. | |
| 5,476,494 A | 12/1995 | Edell et al. | |
| 5,521,957 A | 5/1996 | Hansen | |
| 5,554,187 A | 9/1996 | Rizzo, III | |
| 5,575,813 A | 11/1996 | Edell et al. | |
| 5,597,381 A | 1/1997 | Rizzo, III | |
| 5,636,038 A | 6/1997 | Lynt et al. | |
| 5,642,431 A | 6/1997 | Poggio et al. | |
| 5,777,715 A | 7/1998 | Kruegle et al. | |
| 5,800,530 A | 9/1998 | Rizzo, III | |
| 5,835,616 A | 11/1998 | Lobo et al. | |
| 5,850,470 A | 12/1998 | Kung et al. | |
| 5,875,018 A | 2/1999 | Lamprecht | |
| 5,935,155 A | 8/1999 | Humayun et al. | |
| 6,104,671 A | 8/2000 | Hoyt et al. | |
| 6,115,482 A | 9/2000 | Sears et al. | |
| 6,120,538 A | 9/2000 | Rizzo, III et al. | |
| 6,161,091 A | 12/2000 | Akamine et al. | |
| 6,230,057 B1 | 5/2001 | Chow et al. | |
| 6,324,429 B1 | 11/2001 | Shire et al. | |
| 6,368,349 B1 | 4/2002 | Wyatt et al. | |
| 6,389,317 B1 | 5/2002 | Chow et al. | |
| 6,411,327 B1 | 6/2002 | Kweon et al. | |
| 6,446,041 B1 | 9/2002 | Reynar et al. | |
| 6,470,264 B2 | 10/2002 | Bide | |
| 6,549,122 B2 | 4/2003 | Depta | |
| 6,671,618 B2 | 12/2003 | Hoisko | |
| 6,774,788 B1 | 8/2004 | Balfe | |
| 6,920,358 B2 | 7/2005 | Greenberg et al. | |
| 6,948,937 B2 | 9/2005 | Tretiakoff et al. | |
| 6,976,998 B2 | 12/2005 | Rizzo et al. | |
| 7,295,872 B2 | 11/2007 | Kelly et al. | |
| 7,307,575 B2 | 12/2007 | Zemany | |
| 7,308,315 B2 | 12/2007 | Ohta et al. | |
| 7,565,139 B2 | 7/2009 | Neven, Sr. et al. | |
| 7,598,976 B2 | 10/2009 | Sofer et al. | |
| 7,627,142 B2 | 12/2009 | Kurzweil et al. | |
| 7,642,949 B2 | 1/2010 | Pergande et al. | |
| 7,659,915 B2 | 2/2010 | Kurzweil et al. | |
| 7,782,251 B2 | 8/2010 | Bishop et al. | |
| 7,788,032 B2 | 8/2010 | Moloney | |
| 7,805,307 B2 | 9/2010 | Levin et al. | |
| 7,817,855 B2 | 10/2010 | Yuille et al. | |
| 7,898,468 B2 | 3/2011 | Samaniego et al. | |
| 7,925,354 B2 | 4/2011 | Greenberg et al. | |
| 7,965,196 B2 | 6/2011 | Liebermann | |
| 7,967,439 B2 | 6/2011 | Shelhamer et al. | |
| 7,983,920 B2 | 7/2011 | Sinclair, II | |
| 7,991,576 B2 | 8/2011 | Roumeliotis | |
| 8,009,928 B1 | 8/2011 | Manmatha et al. | |
| 8,014,604 B2 | 9/2011 | Tzadok et al. | |
| 8,015,132 B2 | 9/2011 | Xu | |
| 8,018,580 B2 | 9/2011 | Luo et al. | |
| 8,019,428 B2 | 9/2011 | Greenberg et al. | |
| 8,021,045 B2 | 9/2011 | Foos et al. | |
| 8,036,895 B2 | 10/2011 | Kurzweil et al. | |
| 8,049,680 B2 | 11/2011 | Spruck et al. | |
| 8,068,644 B2 | 11/2011 | Tkacik | |
| 8,113,841 B2 | 2/2012 | Rojas et al. | |
| 8,115,831 B2 | 2/2012 | Rodriquez et al. | |
| 8,130,262 B2 | 3/2012 | Behm et al. | |
| 8,135,217 B2 | 3/2012 | Goktekin et al. | |
| 8,135,227 B2 | 3/2012 | Lewis et al. | |
| 8,139,894 B2 | 3/2012 | Nestares | |
| 8,150,107 B2 | 4/2012 | Kurzweil et al. | |
| 8,154,771 B2 | 4/2012 | Albrecht et al. | |
| 8,160,880 B2 | 4/2012 | Albrecht et al. | |
| 8,174,931 B2 | 5/2012 | Vartanian et al. | |
| 8,175,802 B2 | 5/2012 | Forstall et al. | |
| 8,185,398 B2 | 5/2012 | Anderson et al. | |
| 8,186,581 B2 | 5/2012 | Kurzweil et al. | |
| 8,204,684 B2 | 6/2012 | Forstall et al. | |
| 8,208,729 B2 | 6/2012 | Foss | |
| 8,210,848 B1 | 7/2012 | Beck et al. | |
| 8,218,020 B2 | 7/2012 | Tenchio et al. | |
| 8,218,873 B2 | 7/2012 | Boncyk et al. | |
| 8,218,874 B2 | 7/2012 | Boncyk et al. | |
| 8,224,078 B2 | 7/2012 | Boncyk et al. | |
| 8,224,079 B2 | 7/2012 | Boncyk et al. | |
| 8,233,671 B2 | 7/2012 | Anderson et al. | |
| 8,234,277 B2 | 7/2012 | Thong et al. | |
| 8,239,032 B2 | 8/2012 | Dewhurst | |
| 2001/0056342 A1 | 12/2001 | Piehn et al. | |
| 2002/0111655 A1 | 8/2002 | Scribner | |
| 2002/0111739 A1 | 8/2002 | Jandrell | |
| 2002/0148607 A1 | 10/2002 | Pabst | |
| 2003/0179133 A1 | 9/2003 | Pepin et al. | |
| 2004/0107010 A1 | 6/2004 | King | |
| 2005/0251223 A1 | 11/2005 | Eckmiller | |
| 2006/0050933 A1 | 3/2006 | Adam et al. | |
| 2006/0129308 A1 | 6/2006 | Kates | |
| 2007/0025512 A1 | 2/2007 | Gertsenshteyn et al. | |
| 2007/0211947 A1 | 9/2007 | Tkacik | |
| 2007/0272738 A1 | 11/2007 | Berkun | |
| 2007/0273708 A1 | 11/2007 | Andreasson et al. | |
| 2007/0279497 A1* | 12/2007 | Wada | G03B 5/00 348/208.7 |
| 2008/0037727 A1 | 2/2008 | Sivertsen et al. | |
| 2008/0077196 A1 | 3/2008 | Greenberg et al. | |
| 2008/0120029 A1 | 5/2008 | Zelek et al. | |
| 2008/0136923 A1 | 6/2008 | Inbar et al. | |
| 2008/0154336 A1 | 6/2008 | McClure et al. | |
| 2008/0154337 A1 | 6/2008 | McClure et al. | |
| 2008/0187104 A1 | 8/2008 | Sung et al. | |
| 2008/0275527 A1 | 11/2008 | Greenberg et al. | |
| 2008/0288067 A1 | 11/2008 | Flood | |
| 2009/0002500 A1* | 1/2009 | Kawai | H02N 2/028 348/208.11 |
| 2009/0186321 A1 | 7/2009 | Rojas et al. | |
| 2009/0306741 A1 | 12/2009 | Hogle et al. | |
| 2009/0312817 A1 | 12/2009 | Hogle et al. | |
| 2010/0002204 A1 | 1/2010 | Jung et al. | |
| 2010/0013612 A1 | 1/2010 | Zachman | |
| 2010/0177179 A1 | 7/2010 | Behm et al. | |
| 2010/0201793 A1 | 8/2010 | Kurzweil et al. | |
| 2011/0013896 A1* | 1/2011 | Kawahara | G03B 5/00 396/55 |
| 2011/0034176 A1 | 2/2011 | Lord et al. | |
| 2011/0043644 A1 | 2/2011 | Munger et al. | |
| 2011/0050546 A1 | 3/2011 | Swartz, Jr. et al. | |
| 2011/0091098 A1 | 4/2011 | Yuille et al. | |
| 2011/0092249 A1 | 4/2011 | Evanitsky | |
| 2011/0143816 A1 | 6/2011 | Fischer et al. | |
| 2011/0181745 A1 | 7/2011 | Nagatsuma et al. | |
| 2011/0213664 A1 | 9/2011 | Osterhout et al. | |
| 2011/0214082 A1 | 9/2011 | Osterhout et al. | |
| 2011/0216179 A1 | 9/2011 | Dialameh et al. | |

(56) References Cited

U.S. PATENT DOCUMENTS

| | | |
|---|---|---|
| 2011/0221656 A1 | 9/2011 | Haddick et al. |
| 2011/0221657 A1 | 9/2011 | Haddick et al. |
| 2011/0221658 A1 | 9/2011 | Haddick et al. |
| 2011/0221659 A1 | 9/2011 | King, III et al. |
| 2011/0221668 A1 | 9/2011 | Haddick et al. |
| 2011/0221669 A1 | 9/2011 | Shams et al. |
| 2011/0221670 A1 | 9/2011 | King, III et al. |
| 2011/0221671 A1 | 9/2011 | King, III et al. |
| 2011/0221672 A1 | 9/2011 | Osterhout et al. |
| 2011/0221793 A1 | 9/2011 | King, III et al. |
| 2011/0221896 A1 | 9/2011 | Haddick et al. |
| 2011/0221897 A1 | 9/2011 | Haddick et al. |
| 2011/0222735 A1 | 9/2011 | Imai et al. |
| 2011/0222745 A1 | 9/2011 | Osterhout et al. |
| 2011/0224967 A1 | 9/2011 | Van Schaik |
| 2011/0225536 A1 | 9/2011 | Shams et al. |
| 2011/0229023 A1 | 9/2011 | Jones et al. |
| 2011/0231757 A1 | 9/2011 | Haddick et al. |
| 2011/0267490 A1 | 11/2011 | Göktekin et al. |
| 2011/0279222 A1 | 11/2011 | LeGree |
| 2011/0292204 A1 | 12/2011 | Boncyk et al. |
| 2011/0295742 A1 | 12/2011 | Boncyk et al. |
| 2011/0298723 A1 | 12/2011 | Fleizach et al. |
| 2011/0298939 A1 | 12/2011 | Melikian |
| 2012/0001932 A1 | 1/2012 | Burnett et al. |
| 2012/0002872 A1 | 1/2012 | Boncyk et al. |
| 2012/0028577 A1 | 2/2012 | Rodriguez et al. |
| 2012/0029920 A1 | 2/2012 | Kurzweil et al. |
| 2012/0044338 A1 | 2/2012 | Lee et al. |
| 2012/0046947 A1 | 2/2012 | Fleizach |
| 2012/0053826 A1 | 3/2012 | Slamka |
| 2012/0054796 A1 | 3/2012 | Gagnon et al. |
| 2012/0062357 A1 | 3/2012 | Slamka |
| 2012/0062445 A1 | 3/2012 | Haddick et al. |
| 2012/0075168 A1 | 3/2012 | Osterhout et al. |
| 2012/0080523 A1 | 4/2012 | D'Urso et al. |
| 2012/0081282 A1 | 4/2012 | Chin |
| 2012/0092460 A1 | 4/2012 | Mahoney |
| 2012/0098764 A1 | 4/2012 | Asad et al. |
| 2012/0113019 A1 | 5/2012 | Anderson |
| 2012/0119978 A1 | 5/2012 | Border et al. |
| 2012/0120103 A1 | 5/2012 | Border et al. |
| 2012/0143495 A1 | 6/2012 | Dantu |
| 2012/0147163 A1 | 6/2012 | Kaminsky |
| 2012/0154144 A1 | 6/2012 | Betts et al. |
| 2012/0154561 A1 | 6/2012 | Chari |
| 2012/0163667 A1 | 6/2012 | Boncyk et al. |
| 2012/0163722 A1 | 6/2012 | Boncyk et al. |
| 2012/0179468 A1 | 7/2012 | Nestares |
| 2012/0183941 A1 | 7/2012 | Steinmetz |
| 2012/0194418 A1 | 8/2012 | Osterhout et al. |
| 2012/0194419 A1 | 8/2012 | Osterhout et al. |
| 2012/0194420 A1 | 8/2012 | Osterhout et al. |
| 2012/0194549 A1 | 8/2012 | Osterhout et al. |
| 2012/0194550 A1 | 8/2012 | Osterhout et al. |
| 2012/0194551 A1 | 8/2012 | Osterhout et al. |
| 2012/0194552 A1 | 8/2012 | Osterhout et al. |
| 2012/0194553 A1 | 8/2012 | Osterhout et al. |
| 2012/0195467 A1 | 8/2012 | Boncyk et al. |
| 2012/0195468 A1 | 8/2012 | Boncyk et al. |
| 2012/0200488 A1 | 8/2012 | Osterhout et al. |
| 2012/0200499 A1 | 8/2012 | Osterhout et al. |
| 2012/0200595 A1 | 8/2012 | Lewis et al. |
| 2012/0200601 A1 | 8/2012 | Osterhout et al. |
| 2012/0200724 A1 | 8/2012 | Dua et al. |
| 2012/0206322 A1 | 8/2012 | Osterhout et al. |
| 2012/0206323 A1 | 8/2012 | Osterhout et al. |
| 2012/0206334 A1 | 8/2012 | Osterhout et al. |
| 2012/0206335 A1 | 8/2012 | Osterhout et al. |
| 2012/0206485 A1 | 8/2012 | Osterhout et al. |
| 2012/0212398 A1 | 8/2012 | Border et al. |
| 2012/0212399 A1 | 8/2012 | Border et al. |
| 2012/0212400 A1 | 8/2012 | Border et al. |
| 2012/0212406 A1 | 8/2012 | Osterhout et al. |
| 2012/0212414 A1 | 8/2012 | Osterhout et al. |
| 2012/0212484 A1 | 8/2012 | Haddick et al. |
| 2012/0212499 A1 | 8/2012 | Haddick et al. |
| 2012/0218172 A1 | 8/2012 | Border et al. |
| 2012/0218301 A1 | 8/2012 | Miller |
| 2012/0227812 A1 | 9/2012 | Quinn et al. |
| 2012/0227813 A1 | 9/2012 | Meek et al. |
| 2012/0227820 A1 | 9/2012 | Poster |
| 2012/0235883 A1 | 9/2012 | Border et al. |
| 2012/0235884 A1 | 9/2012 | Miller et al. |
| 2012/0235885 A1 | 9/2012 | Miller et al. |
| 2012/0235886 A1 | 9/2012 | Border et al. |
| 2012/0235887 A1 | 9/2012 | Border et al. |
| 2012/0235900 A1 | 9/2012 | Border et al. |
| 2012/0236030 A1 | 9/2012 | Border et al. |
| 2012/0236031 A1 | 9/2012 | Haddick et al. |
| 2012/0242678 A1 | 9/2012 | Border et al. |
| 2012/0242697 A1 | 9/2012 | Border et al. |
| 2012/0242698 A1 | 9/2012 | Haddick et al. |
| 2012/0249797 A1 | 10/2012 | Haddick et al. |
| 2014/0303687 A1* | 10/2014 | Wall, III .............. A61F 9/08 607/54 |
| 2015/0002808 A1 | 1/2015 | Rizzo, III |

FOREIGN PATENT DOCUMENTS

| | | |
|---|---|---|
| CN | 101791259 | 8/2010 |
| DE | 102008059175 | 5/2010 |
| DE | 102009059820 | 6/2011 |
| EP | 2065871 | 6/2009 |
| EP | 2096614 | 9/2009 |
| EP | 2371339 | 10/2011 |
| EP | 2395495 | 12/2011 |
| JP | 2002-219142 | 8/2002 |
| KR | 10-2003-0015936 | 2/2003 |
| KR | 10-2006-0071507 | 6/2006 |
| WO | WO 97/17043 | 5/1997 |
| WO | WO 97/18523 | 5/1997 |
| WO | WO 98/32044 | 7/1998 |
| WO | WO 98/36793 | 8/1998 |
| WO | WO 98/36795 | 8/1998 |
| WO | WO 98/36796 | 8/1998 |
| WO | WO 98/37691 | 8/1998 |
| WO | WO 98/55833 | 12/1998 |
| WO | WO 01/03635 | 1/2001 |
| WO | WO 02/089053 | 11/2002 |
| WO | WO 03/078929 | 9/2003 |
| WO | WO 03/107039 | 12/2003 |
| WO | WO 2006/083508 | 8/2006 |
| WO | WO 2006/085310 | 8/2006 |
| WO | WO 2007/063360 | 6/2007 |
| WO | WO 2007/095621 | 8/2007 |
| WO | WO 2007/138378 | 12/2007 |
| WO | WO 2008/020362 | 2/2008 |
| WO | WO 2008/052166 | 5/2008 |
| WO | WO 2008/109781 | 9/2008 |
| WO | WO 2008/116288 | 10/2008 |
| WO | WO 2009/154438 | 12/2009 |
| WO | WO 2010/145013 | 1/2010 |
| WO | WO 2010/142689 | 12/2010 |
| WO | WO 2011/017653 | 2/2011 |
| WO | WO 2013/067539 | 5/2013 |

OTHER PUBLICATIONS

International Search Report and Written Opinion in International Application No. PCT/US2012/063577, mailed Feb. 20, 2013, 12 pages.
International Preliminary Report on Patentability in International Application No. PCT/US2012/063577, mailed May 15, 2014, 8 pages.
International Search Report and Written Opinion in International Application No. PCT/US2012/063619, mailed Mar. 29, 2013, 14 pages.
International Preliminary Report on Patentability in International Application No. PCT/US2012/063619, mailed May 15, 2014, 9 pages.
Adjouadi, "A man-machine vision interface for sensing the environment," *J. Rehabilitation Res.* 29(2): 57-76 (1992).

(56) References Cited

OTHER PUBLICATIONS

Censi et al., "Image Stabilization by Features Trading," IEEE International Conference on Image Analysis and Processing, 1999, pp. 665-667.
Chang et al., "Digital image translational and rotational motion stabilization using optimal flow technique," *IEEE Transactions on Consumer Electronics* 48(1): 108-115 (2002).
Chen et al., "Video Stabilization Using a Block-Based Parametric Motion Model," *Stanford University Department of Electrical Engineering Technical Report*, 2000, 32 pages.
Crawford, "Living Without a Balancing Mechanism," *Brit. J. Ophthal.* 48: 357-360 (1964).
Drahansky et al., "Accelerometer Based Digital Video Stabilization for General Security Surveillance Systems," *Int. J. of Security and Its Applications*, 4(1): 1-10 (2010).
Grossman et al., "Frequency and velocity of rotational head perturbations during locomotion," *Exp. Brain Res.* 70: 470-476 (1988).
Grossman et al., "Performance of the Human Vestibuloocular Reflex During Locomotion," *J. Neurophys.* 62(1): 264-272 (1989).
Grossman and Leigh, "Instability of Gaze during Locomotion in Patients with Deficient Vestibular Function," *Ann. Neurol.* 27(5): 528-532 (1990).
Hirasaki et al., "Effects of walking velocity on vertical head and body movements during locomotion," *Exp. Brain Research* 127: 117-130 (1999).
Horn et al., "Time to contact relative to a planar surface," *IEEE Intelligent Vehicles Symposium* 1-3: 45-51 (2007).
Horn et al., "Hierarchical framework for direct gradient-based time-to-contact estimation," *IEEE Intelligent Vehicles Symposium* 1-2: 1394-1400 (2009).
Itti et al., "Computational modelling of visual attention," *Nat. Rev. Neurosci.* 2(3): 194-203 (2001).
Karacs et al., "Bionic Eyeglass: an Audio Guide for Visually Impaired," *IEEE Biomedical Circuits and Systems Conference*, 2006, pp. 190-193.
Quattoni et al., "Recognizing Indoor Scenes," *IEEE Conference on Computer Vision and Pattern Recognition*, 2009, pp. 413-420.
Roska et al., "System aspects of a bionic eyeglass," *Proceedings of the IEEE International Symposium on Circuits and Systems*, 2006, pp. 164-167.
Sachs et al., "Image Stabilization Technology Overview," 2011, downloaded from internet address http://www.invensense.com/mems/gyro/documents/whitepapers/ImageStabilization Whitepaper_051606.pdf, 18 pages.
Turk et al., "Eigenfaces for Recognition," *J. Cognitive Neuroscience* 31(3): 71-86 (1991).
Unknown, "Augmented Reality for the Totally Blind," 2011, downloaded from internet address http://www.seeingwithsound.com, 1 page.
Unknown, "LiDAR Glasses for Blind People," 2011, downloaded from internet address http://blog.lidarnews.com/lidar-glasses-for-blind-people, 1 page.
Uomori et al., "Automatic image stabilizing system by full-digital signal processing," *IEEE Transactions on Consumer Electronics* 36(3): 510-519 (1990).
Viola et al., "Rapid Object Detection using a Boosted Cascade of Simple Features," *IEEE Conference on Computer Vision and Pattern Recognition*, 2001, pp. 511-518.
Wagner et al., "Color Processing in Wearable Bionic Eyeglass," *Proceedings of the 10th IEEE International Workshop on Cellular Neural Networks and Their Applications*, 2006, pp. 1-6.
Xiao et al., "SUN Database: Large Scale Scene Recognition from Abbey to Zoo," *IEEE Conference on Computer Vision and Pattern Recognition*, 2010, pp. 3485-3492.
Zijlstra et al., "Assessment of spatio-temporal gait parameters from trunk accelerations during human walking," *Gait & Posture* 18: 1-10 (2003).
Zöllner et al., "NAVI—Navigational Aids for the Visually Impaired," 2011, downloaded from Internet address http://hci.uni-konstanz.de/blog/2011/03/15/navi/?lang=en, 2 pages.

\* cited by examiner

CONTEXTUAL IMAGE STABILIZATION

CROSS-REFERENCE TO RELATED APPLICATIONS

This application is a national stage application under 35 U.S.C. §371 of PCT Patent Application No. PCT/US2012/063577, filed on Nov. 5, 2012 and published as WO 2013/067513, which claims priority under 35 U.S.C. §119 to U.S. Provisional Application Nos. 61/555,908 and 61/555,930, each filed on Nov. 4, 2011, the entire contents of each of which is incorporated herein by reference.

TECHNICAL FIELD

This disclosure relates to stabilization of detectors used for imaging, and contextual processing of measurement data.

BACKGROUND

When visual information is acquired using a detector mounted to a prosthetic device worn by a patient, the information can include artifacts that reflect involuntary movement of the patient rather than intentional positioning of the detector. These artifacts can limit the usefulness of the acquired visual information. Methods for processing acquired images using various software algorithms in an attempt to reduce such artifacts have been described. As the amount of visual information acquired increases, the hardware requirements for implementing such algorithms to produce relatively rapid results also increase.

SUMMARY

The methods and systems disclosed herein can be used to compensate for motion of a detector while the detector acquires information. While motion of a detector can occur in a variety of circumstances, an important application of the methods and systems disclosed herein involves the use of detectors to provide visual information to persons with reduced visual acuity. In such circumstances, involuntary motion of the detector (as occurs, for example, when a person is wearing the detector while walking or moving their head) can lead to aberrations such as shakiness and blurring of the visual information. As a result, a person receiving the blurred visual information, or other information derived from the visual information, may have difficulty interpreting the information.

The methods and systems disclosed herein can compensate for involuntary motion of a detector. One or more sensors coupled to the detector detect and transmit information about linear and/or angular motion of the detector to an electronic processor. The processor analyzes the motion of the detector, separating the motion into one or more components. Each component is assigned to a particular class by the processor. As used herein, a "class" corresponds to a certain category, type, source, or origin of motion. For example, certain classes of motion correspond to involuntary movement of the detector and are designated for compensation. Other classes of motion are recognized by the electronic processor as corresponding to voluntary movement of the detector (e.g., the movement of the detector that occurs when the wearer shifts his or her gaze), and are not designated for compensation. The electronic processor can then generate control signals that drive actuators to compensate for the components of the motion designated for compensation. The actuators can be coupled to one or more components of the systems including, for example, the detector (e.g., the exterior housing of the detector), one or more sensing elements within the detector (e.g., CCD arrays and/or other sensor elements such as diodes), and one or more optical elements through light from the scene that is being imaged passes (e.g., one or more mirrors, lenses, prisms, optical plates, and/or other such elements). Actuators can also be coupled to more than one component in the system, including any of the foregoing types of components.

In general, in a first aspect, the disclosure features an image stabilization system that includes a detector configured to detect images, an actuator coupled to the detector, a sensor coupled to the detector and configured to detect motion of the detector, and an electronic processor in communication with the sensor and the actuator, where the electronic processor is configured to: (a) receive information about motion of the detector from the sensor; (b) determine components of the motion of the detector, and associate a class with each of the determined components; (c) identify components to be compensated from among the determined components based on the associated classes; and (d) generate a control signal that causes the actuator to adjust a position of at least a portion of the detector to compensate for the identified components.

Embodiments of the system can include any one or more of the following features.

The sensor can include at least one of an accelerometer and a gyroscope. The detector can include a camera. The actuator can include at least one of a mechanical actuator and a piezoelectric actuator.

The motion of the detector can include at least one of motion along a linear direction and angular motion about an axis. The actuator can be configured to adjust the position by at least one of translating and rotating the at least a portion of the detector.

The system can include a support structure to which the detector, actuator, sensor, and electronic processor are attached. The support structure can be eyeglass frames or a hat or cap.

The system can include a receiver in communication with the detector and configured to: (a) receive information from the detector, where the information is derived from one or more images detected by the detector; and (b) transmit a representation of the received information to a human. The receiver can include a visual implant positioned in an eye of the human.

The system can include at least one additional sensor coupled to the detector, where each sensor is configured to detect linear motion along any of three orthogonal axes or angular motion about any one of the three orthogonal axes, and where each sensor detects a different motion of the detector.

The system can be worn by a human, and one of the associated classes can include involuntary motion of the detector by the human. Another one of the classes can include voluntary motion of the detector by the human.

Embodiments of the system can also include any of the other features disclosed herein, in any combination, as appropriate.

In another aspect, the disclosure features a method for image stabilization that includes obtaining image information using a detector, detecting motion of the detector while the image information is obtained, determining components of the motion of the detector and associating a class with each of the determined components, identifying components to be compensated from among the determined components based on the associated classes, and adjusting a position of at least a portion of the detector to compensate for the identified components while the image information is obtained.

Embodiments of the method can include any one or more of the following features, as appropriate.

Obtaining image information can include detecting one or more images.

Detecting motion of the detector can include at least one of detecting a linear displacement of the detector along a direction and detecting an angular displacement of the detector about an axis. Detecting motion of the detector can include at least one of detecting linear displacements of the detector along at least two orthogonal coordinate directions, and detecting angular displacements of the detector about at least two orthogonal axes.

One of the classes can include involuntary motion of the detector by a wearer of the detector. One of the classes can include voluntary motion of the detector by the wearer.

Adjusting the position of at least a portion of the detector to compensate for the identified components can include directing an actuator coupled to the detector to: (a) linearly displace the detector along a direction opposite to a linear displacement corresponding to at least one of the identified components; or (b) angularly displace the detector about an axis in a direction opposite to an angular displacement about the same axis corresponding to at least one of the identified components; or (c) both (a) and (b).

Determining components of the motion of the detector can include detecting a magnitude of a displacement of the detector relative to a reference position, and identifying components of the motion based upon the magnitude of the displacement. The method can include associating a class with at least some of the determined components based upon the magnitude of the displacement.

Determining components of the motion of the detector can include detecting a magnitude of a displacement of the detector relative to a reference position, determining one or more frequencies associated with the displacement of the detector, and identifying components of the motion based upon the one or more frequencies. The method can include associating a class with at least some of the determined components based upon the determined frequencies.

The method can include transmitting the image information from the detector to a receiver. The detector can be worn by a human, and the receiver can be a visual implant positioned in an eye of the human.

The method can include determining a velocity of the detector, and halting transmission of the image information to the receiver when a magnitude of the velocity exceeds a threshold value.

Embodiments of the method can also include any of the other features disclosed herein, in any combination, as appropriate.

In a further aspect, the disclosure features a method for transmitting image information that includes detecting motion of a detector while the detector measures image information, decomposing the detected motion into a plurality of components to identify a portion of the motion to be compensated based on at least one of a magnitude, a frequency, and a velocity of the motion, and while the detector measures image information: (a) moving the detector to offset the identified portion of the motion; and (b) transmitting information derived from the image information to a receiver.

Embodiments of the method can include any one or more of the features disclosed herein, in any combination, as appropriate.

In another aspect, the disclosure features a method for image correction that includes obtaining an image using a detector, detecting motion of the detector while the image is obtained, transmitting information about the motion of the detector to an electronic processor, and using the electronic processor to correct the image based on the information about the motion of the detector.

Embodiments of the method can include any one or more of the following features.

Correcting the image can include reducing artifacts in the image that arise from the motion of the detector.

The method can include: determining components of the motion of the detector and associating a class with each of the determined components; identifying components to be compensated from among the determined components based on the associated classes; and correcting the image by compensating for the effects of the identified components in the image.

Embodiments of the method can also include any of the other features disclosed herein, in any combination, as appropriate.

Unless otherwise defined, all technical and scientific terms used herein have the same meaning as commonly understood by one of ordinary skill in the art to which this invention belongs. Although methods and materials similar or equivalent to those described herein can be used in the practice or testing of the disclosed embodiments, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages of the invention will be apparent from the description, drawings, and claims.

DESCRIPTION OF DRAWINGS

Like reference symbols in the various drawings indicate like elements.

DETAILED DESCRIPTION

Introduction

Figure 1:
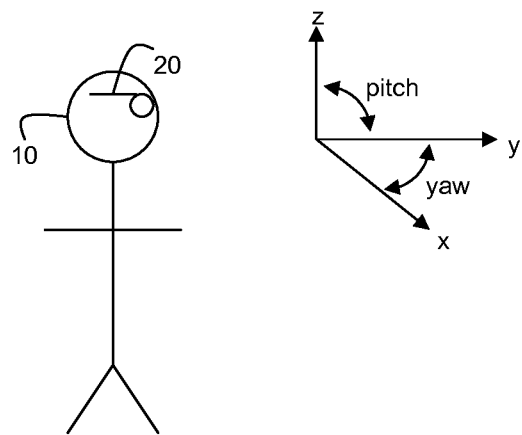
FIG. 1 is a schematic diagram of a person undergoing locomotion.

Compensating for the motion of a detector during data acquisition is a problem that is common to a variety of different applications. Visual information such as still or video images is particularly prone to aberrations such as shakiness and blurring that result from motion of the detector as the information is obtained. Attempts to compensate for detector motion during the acquisition of visual information have generally involved increasingly sophisticated software methods for analyzing and numerically processing images after they are acquired. However, as the information density in the acquired images increases, the computing hardware requirements for implementing complex image processing algorithms so that they execute within a reasonable time also must increase. Moreover, more advanced hardware tends to be larger, to consume more power, and to be unsuitable for implementation in portable applications. Thus, alternatives for image stabilization to known image processing algorithms are needed.

Human visual impairment is a significant handicap that dramatically alters the quality of life for an affected person. In recent years, efforts toward enhancing the visual acuity of persons with visual impairment have focused on methods for artificially acquiring and conveying visual information in a manner that can be interpreted by such persons. This disclosure features systems for providing such visual information, and other types of information derived from visual information, that can be housed in a variety of wearable prosthetics such as eyeglass frames. The systems typically feature one or more detectors configured to acquire visual information and to transmit that information to the wearer of the prosthetic device.

The methods and systems disclosed herein provide for compensation of visual information by directly compensating for the motion of the detector as the visual information is acquired. In this way, the visual information is already compensated when it is acquired, and no post-acquisition processing is necessary. As a result, the computing hardware requirements and power consumption of the systems disclosed herein are, in general, significantly reduced compared to systems that rely on software-based post-processing of visual information. However, the present systems can also be combined with known image stabilization software systems. For example, the sensors disclosed herein can be used to estimate the motion of one or more detectors, rather than using only software-based image processing algorithms to perform this estimation, as is common in conventional motion compensation systems. Typically, estimation of detector motion using image processing algorithms creates a feedback "bottleneck," limiting the rate at which information can be provided to the wearer of such systems. The systems and methods disclosed herein allow this processing bottleneck to be largely circumvented, making real-time or near-real-time motion compensation feasible.

Systems for Motion Compensation During Active Detection

To implement motion compensation of a detector, however, it can be important to determine the context in which the motion occurs. By determining the proper context of the motion, the systems and methods disclosed herein can selectively compensate for certain types of motion, and not compensate for other types of motion. Further, the systems and methods disclosed herein can deliver visual information to a person that is appropriate to the context in which the information will be used. As an example, consider the case of a visually impaired person wearing a visual detector and undergoing locomotion (e.g., walking). FIG. 1 shows a schematic diagram of the person's head 10 relative to a coordinate system describing the locomotion. Suppose the person in FIG. 1 walks along a direction parallel to the y-coordinate direction. As locomotion occurs, involuntary movement of the person's head 10 also occurs. In particular, linear back-and-forth motion of the person's head 10 occurs in a direction parallel to the y-coordinate direction. Linear up-and-down motion of the person's head 10 also generally occurs in a direction parallel to the z-coordinate direction. Further, angular side-to-side motion of the person's head 10 generally occurs in the x-y plane (referred to as "yaw" motion), and angular up-and-down motion of the person's head 10 generally occurs in the y-z plane (referred to as "pitch" motion). All of these components of the motion of the person's head 10 are typically involuntary.

For a person undergoing locomotion to navigate reliably based on visual information obtained by prosthetic device 20, a detector in prosthetic device 20 that measures the visual information should remain stably fixed upon a particular scene of interest. However, as discussed above, visual information measured by prosthetic device 20 will typically include artifacts that result from involuntary motion of the person's head 10 during acquisition of the information. Such artifacts can make the visual information difficult to interpret for the person receiving it. A similar effect referred to as oscillopsia has been observed in sighted persons who lose their ability to stabilize their gaze in space due to the loss of inner ear balance and vestibular function. To avoid such problems, involuntary components of the motion of the detector in prosthetic device 20 (which are the result of involuntary components of the motion of the person's head 10) are compensated by the systems and methods disclosed herein, so that the visual information provided to the person wearing the prosthetic device reflects a "steady gaze" of the detector on a scene of interest.

On the other hand, consider the case where a person at rest slowly turns his or her head (thereby moving the detector located in prosthetic device 20) to look at an object of interest. In this example, compensating for the motion of the detector is counterproductive, because the movement of the detector is intended by the wearer—it is not involuntary. Compensating for such motion frustrates the intent of the wearer, which is to change the orientation of the detector and thereby alter the nature of the visual information that is acquired.

To provide visual information that is appropriate to a person in a wide variety of circumstances, the systems and methods disclosed herein implement context-dependent compensation of acquired information. That is, the systems and methods measure the motion of one or more detectors used to acquire visual information, analyze the components of the motion of the detectors to determine the context of each component of the motion, and then compensate only the components of motion that are appropriate for compensation. Whether or not it is appropriate to compensate a particular component of motion depends on the context under which that component of motion arises. For example, involuntary movements of a detector are typically compensated, whereas voluntary (e.g., on the part of the wearer of the prosthetic device) movements of the detector are not compensated.

In this way, the systems and methods disclosed herein bear some similarities to the natural methods by which the brain perceives information. When a person is walking, for example, the brain ensures that involuntary head bobbing and translation are compensated by rapid countervailing movements of the eyes, so that the person's gaze remains fixed on a particular scene. A similar type of compensation occurs when a person nods his or her head to indicate "yes" or "no"—the person's gaze generally remains fixed on a particular scene through compensating movements of the eyes which are initiated by the brain. In contrast, when a person rapidly turns his or her head sideways (e.g., to follow a moving object), the brain generally does not compensate the acquired visual information for the motion, and the visual information that is perceived by the person typically is blurred as a result.

Figure 2:
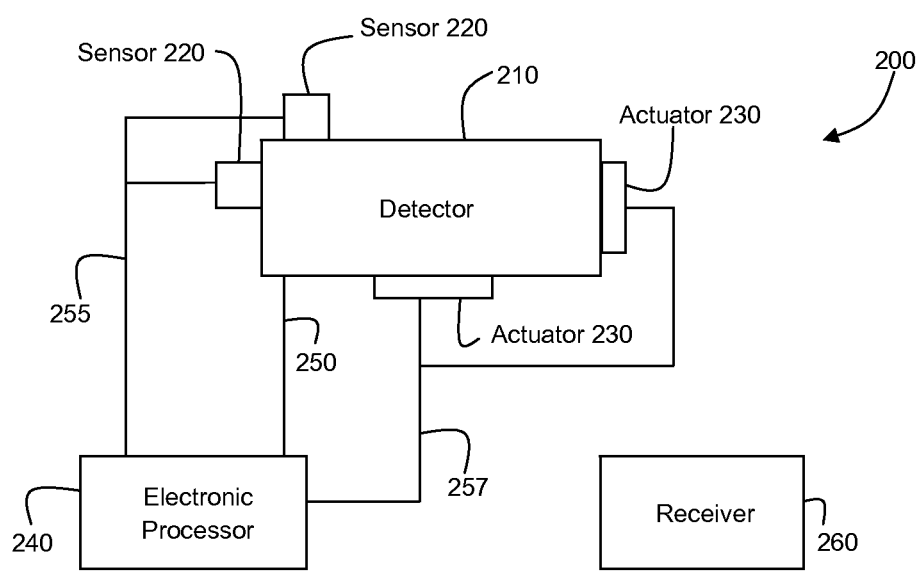
FIG. 2 is a schematic diagram of a system for acquiring information with a detector that is actively compensated.

FIG. 2 shows a schematic diagram of an embodiment of a system 200 for providing visual information to a person (or even to an animal). System 200 includes a detector 210, sensors 220, actuators 230, and an electronic processor 240 coupled to detector 210 via communication line 250. System 200 can optionally include a receiver 260.

Detector 210 can generally include one or more detectors configured to acquire visual information. Suitable detectors include CCD cameras, CMOS-based detectors, analog imaging devices, diode arrays, and other detectors capable of obtaining visual information and, more generally, measuring optical signals.

System 200 can include one or more sensors 220. Although FIG. 2 shows a system with two sensors, more generally system 200 can include any number of sensors. Sensors 220 are configured to detect motion of detector 210. In particular, referring to FIG. 1, sensors 220 can be configured to detect linear motion of detector 210 (e.g., back-and-forth linear motion parallel to the y-coordinate direction and/or up-and-down linear motion parallel to the z-coordinate direction). Sensors 220 can also be configured to detect angular motion of detector 210 (e.g., angular yaw motion in the x-y plane and/or angular pitch motion in the y-z plane). Sensors 220 communicate information about the motion of detector 210 to electronic processor 240 via communication line 255.

A variety of different types of sensors can be used to detect motion of detector 210. In some embodiments, for example, sensors 220 include accelerometers configured to detect linear motion of detector 210. In certain embodiments, sensors 220 include gyroscopes configured to detect angular motion of detector 210. Other sensors that can be used to detect motion of detector 210 include: magnetometers, which measure angular yaw motion of detector 210 by sensing magnetic field changes; and global positioning system (GPS) detectors. In some embodiments, sensors that include multiple different types of detectors can be used to detect motion of detector 210. For example, commercially available inertial measurement units (IMUs) can be used to detect motion of detector 210. One commercially available IMU that can be used in the systems and methods disclosed herein is the Six Degrees of Freedom Inertial Sensor ADIS16385 (available from Analog Devices Inc., Norwood, Mass.) which includes three accelerometers and three gyroscopes in a single integrated package, and can be used to detect roll, pitch, and yaw angular motions of detector 210, and also acceleration in each of three orthogonal coordinate directions. Other commercially available IMUs that can be used in the systems and methods disclosed herein include the MPU-600 Motion Processor, available from InvenSense (Sunnyvale, Calif.), and the Ten Degrees of Freedom Inertial Sensor AIS16407 (available from Analog Devices Inc.).

Actuators 230 are coupled to detector 210 and configured to adjust the position of detector 210 by receiving control signals from electronic processor 240 via communication line 257. Although system 200 in FIG. 2 includes two actuators 230, more generally system 200 can include any number of actuators (for example, to fully compensate the motion of detector 210, system 200 can include six actuators, three of which translate detector 210 in mutually orthogonal coordinate directions, and the other three that rotate detector 210 about each of the coordinate directions). By adjusting the position of detector 210, actuators 230 are capable of compensating for involuntary motion of detector 210 when the detector is moved involuntarily, e.g., when worn by a person. Referring to FIG. 1 for example, actuators 230 are capable of compensating both linear and angular motion of detector 210 when a person wearing detector 210 undergoes locomotion. In general, a wide variety of different types of actuators 230 can be used in system 200, including motorized actuators, piezoelectric actuators, electrostrictive actuators, and any other types of actuators that can be controlled by electronic processor 240. For example, motorized actuators that can be used include the E-flite 7.5 Gram Sub-Micro S75 Servo (available from Horizon Hobby, Inc., Champaign, Ill.).

In some embodiments, system 200 includes receiver 260. Receiver 260 is generally configured to receive acquired visual information from detector 210, either via a communication line linking detector 210 and receiver 260, or through another communications interface (such as a wireless communications interface). Receiver 260 can also be configured to receive information from external sources such as other computing devices; in some embodiments, detector 210 provides visual information to an external device, which then processes the visual information and relays a portion of the processed information to receiver 260.

Receiver 260 can take a variety of different forms. In some embodiments, for example, receiver 260 can be a visual implant that receives visual information and transforms the visual information into electronic signals that can be interpreted as images by the implant wearer. In certain embodiments, receiver 260 can be a device that receives visual or other information and transforms the information into other types of signals such as sounds, speech, vibrations, and/or other non-image visual cues (e.g., flashing lights and other visual signals that convey information or warnings to the wearer). Examples of useful receivers are disclosed, for example, in U.S. Pat. No. 5,935,155, and at the internet address seeingwithsound.com, the entire contents of which are incorporated herein by reference. Certain receivers can also include tactile vibrators such as the C2 tactor (available from EAI, Casselberry, Fla.).

Context-Based Compensation Methods and Systems

Figure 3:
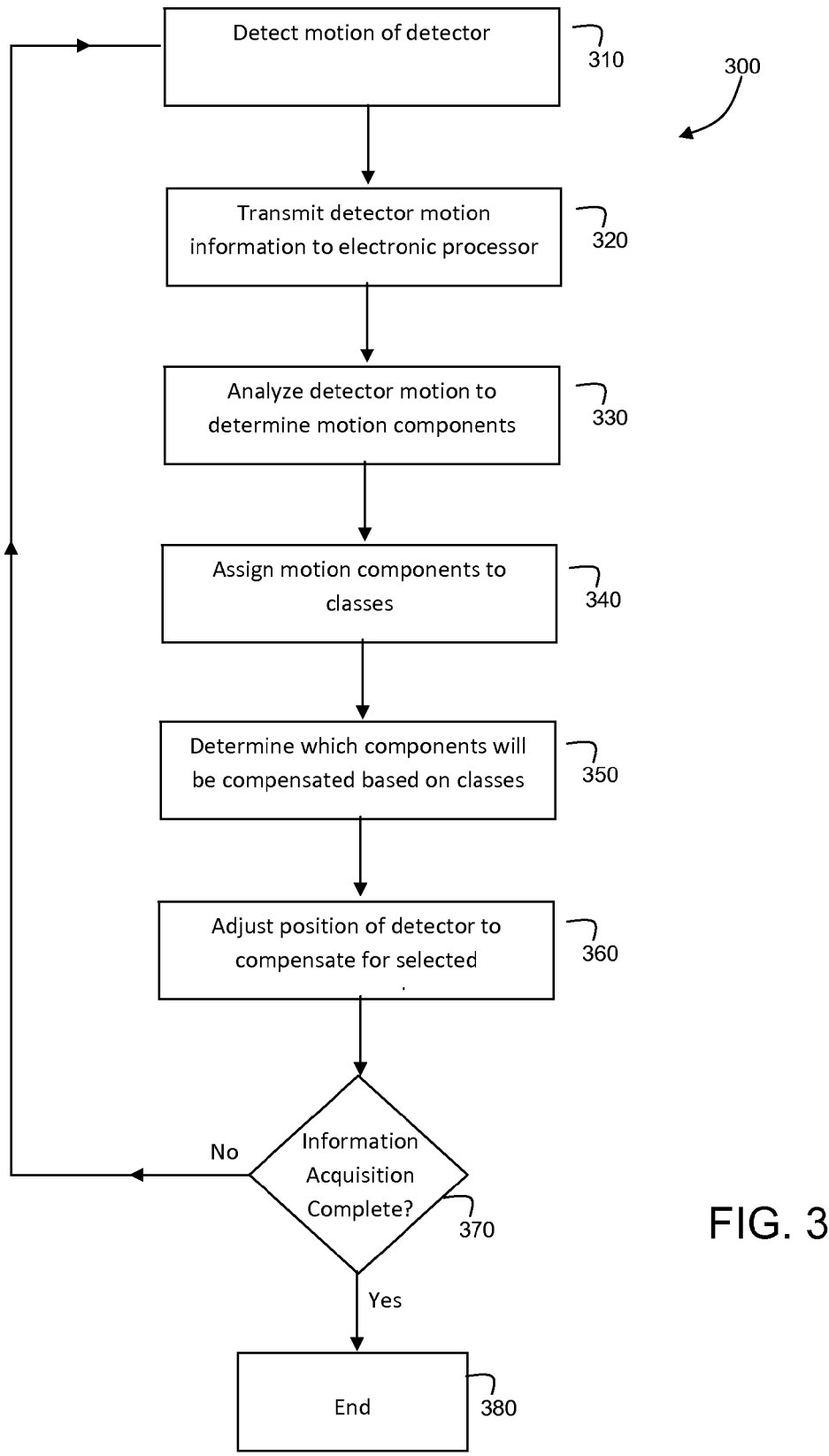
FIG. 3 is a schematic diagram of a flow chart that includes steps for context-based compensation of the motion of a detector during information acquisition.

FIG. 3 shows a flow chart 300 that includes a series of steps for context-based compensation for the motion of detector 210 during acquisition of information. The steps shown in flow chart 300 generally occur while detector 210 acquires information; flow chart 300 therefore represents an active feedback loop that provides dynamic compensation for detector 210. In the first step 310, one or more sensors 220 detect motion (or the absence of motion) of detector 210. Sensors 220 can, in general, detect a variety of different types of motion, including linear motion (e.g., parallel to a particular coordinate direction) and angular motion (e.g., about a stationary axial direction). Information about the motion of detector 210 during information acquisition is transmitted to electronic processor 240 in step 320.

Steps 330, 340, and 350 in flow chart 300 provide for context-based analysis of the motion of detector 210. In step 330, electronic processor 240 analyzes the motion of detector 240 to identify various components of the detector motion. In some embodiments, the identification of different components of the detector's motion is analogous to identifying the causes or the context underlying the detector's motion.

Components of the detector's motion can be identified by analyzing the specific patterns of detector motion detected by sensors 220. As an example, when detector 210 is worn by a person, high-velocity and small-amplitude motions of detector 210 are likely to correspond to involuntary motion as occurs, for example, when the person undergoes locomotion. In contrast, larger-amplitude low-velocity motions of detector 210 are likely to correspond to voluntary motion as occurs, for example, when the person intentionally turns his or her head to shift gaze. On the basis of these principles, electronic processor 240 can analyze the detected motion of detector 210 to identify the various components of the detector's motion in step 330. Then, in step 340, the electronic processor can assign the various motion components to classes. For a system configured to acquire visual information, the classes typically correspond to different contexts or causes of the detector motion.

In general, electronic processor 240 can be configured to identify many different components of motion and to assign the identified components to many different classes or contexts. Three exemplary classes will be discussed below. The first such class or context is motion of a detector due to locomotion by a person wearing or carrying the detector on his or her head. When a person undergoes locomotion, the person's head translates up and down (e.g., parallel to the z-coordinate direction in FIG. 1), pitches forward and backward (e.g., undergoes angular motion in the pitch direction), and rotates from side to side (e.g., undergoes angular motion in the yaw direction). These small-amplitude, high-frequency movements of the head, if uncompensated, would lead to blurred vision in a person with normal visual acuity. Similarly, visual information obtained by a head-mounted detector would also contain artifacts due to motion of the head while the information is acquired.

In individuals with normal visual acuity, the brain eliminates the blurring effects of locomotion through the linear vestibulo-ocular reflex (lVOR) and the angular vestibulo-ocular reflex (aVOR) to compensate for linear and angular head motion, respectively. In general, the relative contributions of the lVOR and aVOR depend upon the distance of the objects that are viewed. The aVOR is typically more significant for objects in the far field (e.g., more than about 1 meter away), while the lVOR is typically more significant for objects in the near field (e.g., closer than 1 meter).

System 200 is typically configured to acquire information in a far field imaging configuration; as such, compensation for linear motion of detector 210 during locomotion usually provides only a marginal benefit to the wearer. However, compensation for pitch and yaw angular motion of detector 210 (which is analogous to the brain's activation of the aVOR reflex) can significantly reduce blurring of the visual information that is acquired by detector 210.

Figure 4A:
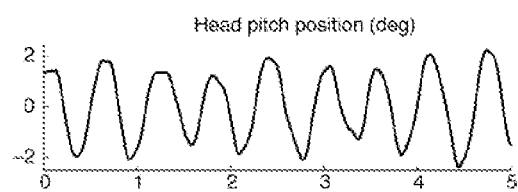
FIG. 4A is a graph of pitch angular motion as a function for time for a detector mounted to a person undergoing locomotion.
Figure 4B:
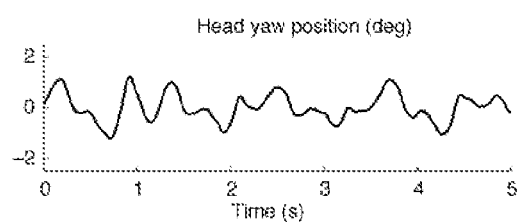
FIG. 4B is a graph of yaw angular motion as a function for time for a detector mounted to a person undergoing locomotion.

FIGS. 4A and 4B show the pitch and yaw angular motion, respectively, of the head of a test subject walking at a speed of approximately 1 m/s. In both figures, the angular displacement of the subject's head is plotted as a function of time. As shown in FIG. 4A, the pitch angular motion is nearly sinusoidal, with a regular angular frequency corresponding to the "bobbing" of the subject's head up and down during locomotion. In FIG. 4B, the yaw angular motion shows a more complex—but still relatively reproducible—angular displacement pattern corresponding to the side-to-side shaking of the subject's head during locomotion.

In step 330 of flow chart 300, electronic processor 240 analyzes the detector motion to identify components of the detector motion. To identify components of the detector motion, electronic processor 240 can, in general, analyze either or both of the measured motions in FIGS. 4A and 4B. In FIG. 4A, for example, electronic processor 240 can perform a Fourier transform analysis or a frequency measurement to determine the frequency of the pitch angular motion, and then identify the motion in FIG. 4A as consisting of a single component. Alternatively, or in addition, electronic processor 240 can compare the measured pitch angular motion in FIG. 4A to a stored reference information describing typical pitch angular motion of the subject's head during locomotion to determine that the measured pitch angular motion represents contributions from a single component.

Electronic processor 240 can analyze the yaw angular motion of detector 210 shown in FIG. 4B in similar fashion. For example, electronic processor 240 can perform a Fourier transform analysis and/or frequency measurement on the yaw angular motion. The yaw angular motion is more complex than the pitch angular motion, and therefore a Fourier transform analysis or frequency measurement will identify more than one frequency present; nonetheless, by comparing the identified frequencies to stored reference information describing the frequencies of typical yaw angular motion of the subject's head, electronic processor 240 can still determine (e.g., from the numerical values and amplitudes of the frequencies present) that the yaw angular motion represents contributions from a single component. Alternatively, or in addition, electronic processor 240 can directly compare the measured yaw angular motion of detector 210 to stored reference information describing typical yaw angular motion of the subject's head during locomotion to determine that the measured motion corresponds to a single motion component.

In step 340, electronic processor 240 assigns the identified components of the detector's motion to classes. In some embodiments, step 340 can be performed essentially contemporaneously with step 330. For example, referring again to FIG. 4A, electronic processor 240 determines in step 330 that the pitch angular motion of detector 210 contains a single motion component, as disclosed above. By comparing the frequency, the amplitude (which corresponds to the displacement of detector 210 relative to a reference position), or the frequency and amplitude of the pitch angular motion in FIG. 4A to reference information describing pitch angular motion of the subject's head during locomotion, electronic processor 240 can assign the component of motion shown in FIG. 4A to the class "locomotion." In other words, electronic processor 240 can determine that the component of the detector's motion shown in FIG. 4A corresponds to motion that occurs in the context of locomotion by the subject (and not in the context of another type of movement such as head nodding or gaze shifting, for example).

Electronic processor 240 can perform a similar assignment based on the yaw angular motion shown in FIG. 4B. As above, determining that the yaw angular motion corresponds to a single component and assigning that component to the class "locomotion" (which is analogous to identifying that the context in which the motion in FIG. 4B arises is when the subject is walking) are steps that can be performed contemporaneously. Electronic processor 240 can, for example, compare the amplitude and/or frequency content of the yaw angular motion in FIG. 4B with reference information and/or stored threshold values for these parameters to determine not only that a single motion component is present, but that the single component arises in the context of locomotion by the subject, and not in the context of another type of movement. Accordingly, electronic processor 240 assigns the motion component plotted in FIG. 4B to the class "locomotion."

Figure 5A:
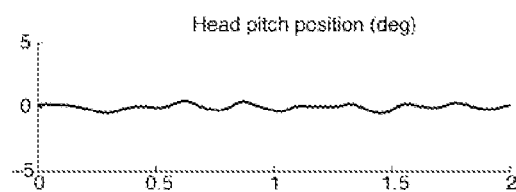
FIG. 5A is a graph of pitch angular momentum as a function of time for a detector mounted to a person shaking his or her head.
Figure 5B:
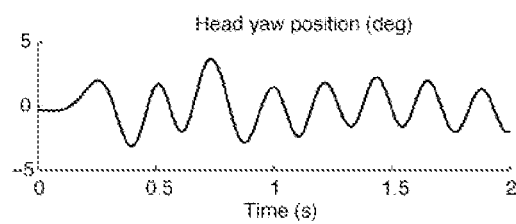
FIG. 5B is a graph of yaw angular momentum as a function of time for a detector mounted to a person shaking his or her head.

A second exemplary class or context of motion corresponds to a subject wearing detector 210 on his or her head and shaking the head from side-to-side to indicate disagreement. FIGS. 5A and 5B show the measured pitch and yaw angular motion, respectively, in this context. Note that in FIGS. 5A and 5B, the subject is stationary and not undergoing locomotion. As shown in FIG. 5A, head shaking produces very little pitch angular motion—in practical terms, not enough to cause significant artifacts in visual information measured by detector 210. However, as shown in FIG. 5B, head shaking produces significant yaw angular motion which, if not compensated, will cause substantial distortion of acquired visual information. For a person with ordinary visual acuity, the brain would activate its aVOR to stabilize the person's gaze during head shaking so that the person's eyes could remain clearly fixed on a particular subject or scene as his or her head shakes from side-to-side.

Returning to flow chart 300, in step 330, electronic processor 240 analyzes FIGS. 5A and 5B to identify components of the motion of detector 210, and in step 340, the electronic processor assigns the identified components to classes. In FIG. 5A, by analyzing the amplitude of measured pitch angular motion, electronic processor 240 determines that the amount of pitch angular motion is insignificant; that is, there is no component of the detector motion to identify. In contrast, in FIG. 5B, electronic processor 240 can analyze both the amplitude and frequency of the yaw angular motion. By comparing the analysis results to stored reference information and/or threshold values, for example, electronic processor 240 can identify a single component of motion present in FIG. 5B, and can assign that component to the class of "head shaking" (e.g., the component of the detector motion occurs in the context of the subject shaking his or her head). Comparing the yaw angular motion in FIG. 5B to the yaw angular motion in FIG. 4B, for example, it is evident that the angular motion in FIG. 5B has a higher frequency than in FIG. 4B, and also a larger amplitude. Thus, in step 340, electronic processor 240—on the basis of these differences—can assign the yaw angular motion in FIG. 4B to the class "locomotion," and can assign the yaw angular motion in FIG. 5B to the class "head shaking."

Figure 6A:
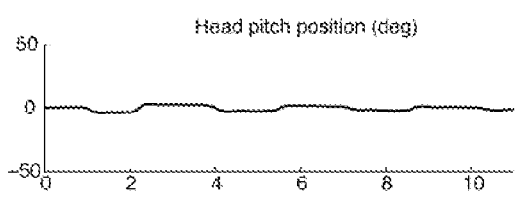
FIG. 6A is a graph of pitch angular momentum as a function of time for a detector mounted to a person undertaking a gaze shift.
Figure 6B:
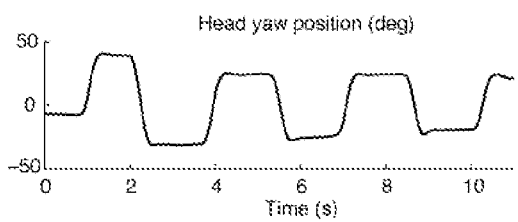
FIG. 6B is a graph of yaw angular momentum as a function of time for a detector mounted to a person undertaking a gaze shift.

A third exemplary class or context of motion corresponds to a gaze shift (e.g., an intentional rotation of the head) by a subject wearing detector 210 on his or her head. FIGS. 6A and 6B show measured pitch and yaw angular motion of the detector during a series of gaze shifts. As shown in FIG. 6A, very little motion in the pitch angular direction is detected; this situation is similar to pitch angular motion during the "head shaking" class of motion depicted in FIG. 5A. However, the series of gaze shifts produces a regular pattern of yaw angular motion, as shown in FIG. 6B.

Returning to flow chart 300, the motion in FIGS. 6A and 6B is analyzed in step 330 to identify motion components, and then the motion components are assigned to classes in step 340. By analyzing the amplitude of the motion in FIG. 6A, electronic processor 240 can readily determine that there are no components of motion present in the pitch angular motion. In contrast, by analyzing the amplitude, frequency, and shape of the yaw angular motion FIG. 6B, and by comparing the analysis results to stored reference information, electronic processor 240 can determine that a single motion component exists in the measured yaw angular motion, and can assign the identified component to the class "gaze shift" (e.g., the motion arises in the context of repeated gaze shifts by the subject). The component of yaw angular motion shown in FIG. 6B can be distinguished from the components shown in FIGS. 4B and 5B according to multiple criteria. For example, the significantly larger amplitude of the yaw motion in FIG. 6B relative to FIGS. 4B and 5B can be used to distinguish the components. Further, the shape and frequency of the recurring pattern of angular displacements in FIG. 6B (e.g., a "square wave" pattern of relatively low frequency) is readily distinguished from the more sinusoidal, higher-frequency patterns of the yaw angular displacements in FIGS. 4A and 5B.

The preceding discussion has provided examples of three different classes or contexts of motion of detector 210 that can be identified by electronic processor 240. In general, however, electronic processor 240 can be configured to identify any number of classes of motion. Moreover, electronic processor 240 can identify and distinguish motion components and assign the components to different classes when multiple different classes of motion give rise to the overall motion of detector 210. For example, in circumstances where the wearer of a head-mounted detector 210 is undergoing locomotion and shaking his or her head from side-to-side at the same time, the measured pitch angular motion of the detector will correspond approximately to a superposition of the motions shown in FIGS. 4A and 5A, and the measured yaw angular motion of the detector will correspond approximately to a superposition of the motions shown in FIGS. 4B and 5B. In these circumstances, electronic processor 240 can analyze the pitch and yaw angular motions to identify components contributing to the angular motions, and can assign the identified components to appropriate classes (e.g., "locomotion" and "head shaking").

As disclosed previously, methods such as Fourier analysis, frequency measurement, and direct comparison to reference information (e.g., by performing a correlation analysis) can be used to identify motion components. These methods can be used when one or more components contribute to a particular measured motion. Other methods can also be used to identify components, and some methods may be more effective at identifying components as the number of components contributing to the measured motion of the detector increases. For example, more sophisticated methods of identifying components such as wavelet analysis, eigenvector decomposition, and principal components analysis can be used by electronic processor 240 to analyze the detector motion.

Returning to flow chart 300, after the motion components have been identified and assigned to classes, electronic processor 240 determines which components of the motion will be compensated based on the classes in step 350. That is, the compensation that is subsequently applied to detector 210 is dependent upon the contextual analysis of the motion of the detector in steps 330 and 340. The determination as to which of the identified components will be compensated is facilitated by stored information in system 200 that describes which classes of motion are suitable for compensation and which are not. This type of information corresponds, in essence, to a set of rules that attempts to mimic the response of a person with ordinary visual acuity.

For example, when a person with ordinary visual acuity undergoes locomotion, the person's brain activates its aVOR to counteract pitch and yaw angular motions of the head, steadying the person's gaze. Thus, in some embodiments, system 200 includes stored information instructing electronic processor 240 to compensate identified components of motion of detector 210 that correspond to the class "locomotion." In so doing, system 200 mimics the visual response of a person with ordinary visual acuity.

When a person with ordinary visual acuity shakes his or her head from side-to-side, the person's brain typically activates its aVOR to counteract the yaw angular motion of the head. However, when the same person shifts his or her gaze from side-to-side, the brain does not typically activate the aVOR (or activates it to a lesser degree). As a result, the vision of even a person with ordinary visual acuity will be blurred somewhat as that person shifts gaze. In similar fashion, in certain embodiments, system 200 includes stored information instructing electronic processor 240 to compensate identified components of motion of detector 210 that are assigned to the class "head shaking," but not to compensate components that are assigned to the class "gaze shift." In this way, system 200 further mimics the visual response of a person with normal visual acuity.

Figure 4C:
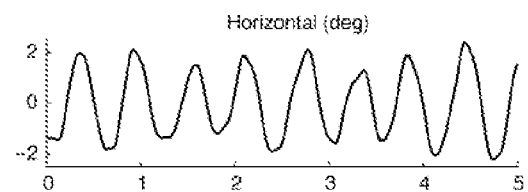
FIG. 4C is a graph of a compensation signal to counteract the motion of the detector in FIG. 4A.
Figure 4D:
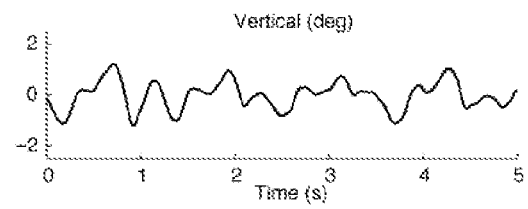
FIG. 4D is a graph of a compensation signal to counteract the motion of the detector in FIG. 4B.

After the components of motion to be compensated have been identified in step 350, electronic processor 240 adjusts the position of detector 210 in step 360 to compensate for the identified components of motion. To perform the position adjustment, electronic processor 240 generates control signals for actuators 230 and transmits the control signals to the actuators via communication line 257. The control signals direct actuators 230 to adjust the position of detector 210 so that some or all of the detector motion (e.g., the components of the motion identified in step 350) is counteracted. FIGS. 4C and 4D show signals generated by electronic processor 240 and transmitted to actuators 230 to compensate for the pitch and yaw angular motions in FIGS. 4A and 4B that correspond to the "locomotion" class. Both the pitch and yaw angular motions were identified for compensation in step 350, and the compensation signals in FIGS. 4C and 4D, respectively, essentially correspond to the inverses of the motions in FIGS. 4A and 4B.

Figure 5C:
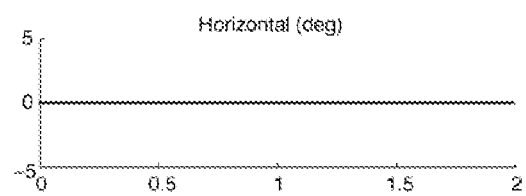
FIG. 5C is a graph of a compensation signal to counteract the motion of the detector in FIG. 5A.
Figure 5D:
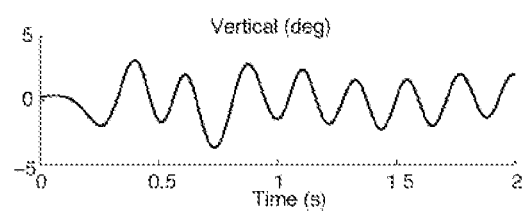
FIG. 5D is a graph of a compensation signal to counteract the motion of the detector in FIG. 5B.

Similarly, the "head shaking" class of motion components was identified for compensation in step 350. Accordingly, the signals shown in FIGS. 5C and 5D transmitted to actuators 230 compensate for the pitch and yaw angular motions shown in FIGS. 5A and 5B, respectively. Because the pitch angular motion is of such small amplitude in FIG. 5A, the corresponding compensation signal in FIG. 5C is also of small amplitude. The compensation signal in FIG. 5D is essentially the inverse of the measured yaw angular motion in FIG. 5B.

Figure 6C:
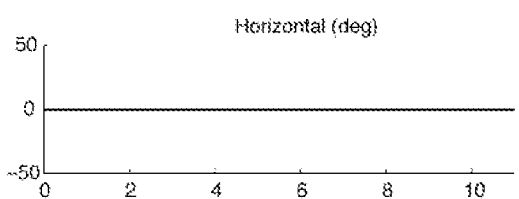
FIG. 6C is a graph of a compensation signal to counteract the motion of the detector in FIG. 6A.
Figure 6D:
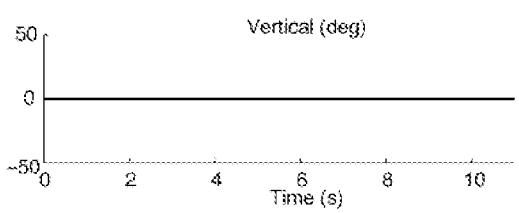
FIG. 6D is a graph of a compensation signal to counteract the motion of the detector in FIG. 6B.

FIGS. 6C and 6D correspond to the compensation signals for the pitch and yaw angular motions associated with the "gaze shift" class in FIGS. 6A and 6B, respectively. The pitch angular motion in FIG. 6A is of small amplitude, and so the corresponding compensation signal in FIG. 6C is also of small amplitude. The yaw angular motion in FIG. 6B is of large amplitude. However, as shown in FIG. 6D, the corresponding compensation signal is of zero amplitude. This situation arises because system 200 is configured to mimic the response of a person with ordinary visual acuity. As disclosed previously, when such a person shifts his or her gaze, the brain generally does not activate its aVOR to a sufficient degree to compensate for the yaw angular motion, and the person's visual perception is blurred. System 200 operates in a similar fashion. By not generating a compensation signal as shown in FIG. 6D, the visual information obtained by detector 210 during a gaze shift by the subject wearing the detector will be subject to distortion; the visual information conveyed to the subject will therefore be blurred in a manner similar to the blurring experienced by a person with normal visual acuity.

In some embodiments, when certain types of motion such as a gaze shift occur and are identified by electronic processor 240 as disclosed herein, system 200 can temporarily halt transmission of visual information from detector 210 to the wearer. For example, in certain embodiments, electronic processor 240 can be configured to determine the speed at which the detector moves during a gaze shift from the position of detector 210 as a function of time. Electronic processor 240 can instruct detector 210 to halt transmission of visual information of the speed of the detector exceeds a certain threshold value because at greater speeds, the visual information may be so distorted that it would only confuse the wearer. Transmission of visual information can be resumed when electronic processor 240 determines that the speed at which the detector moves is reduced below the threshold (e.g., when the gaze shift is completed).

After adjustments to the position of detector 210 have been completed in step 360, the system determines in step 370 whether acquisition of information by detector 210 is complete. If detector 210 is still acquiring information, control returns to step 310, where motion of the detector is again detected, and a new compensation cycle begins. If acquisition of information is complete, the process terminates at step 380.

FIGS. 4A, 4B, 5A, 5B, 6A, and 6B show measured pitch and yaw angular movements of detector 210. Electronic processor 240 is configured to analyze these motions of the detector to generate compensation signals. More generally, however, other movements of detector 210 can also be analyzed to identify motion components that can then be assigned to classes and compensated by system 200. In particular, linear movements of detector 210—such as up-and-down linear motion of detector 210 in a direction parallel to the z-coordinate axis, and forward-and-back linear motion of detector 210 in a direction parallel to the y-coordinate axis—can be analyzed in place of, or in addition to, angular motion of the detector. Amplitudes, frequencies, and functional forms of detector motion along these directions can be analyzed to determine different components of detector motion and determine the context in which each component arises. In some embodiments, angular and linear motions of detector 210 can each include components that correspond to the same class; in such cases, electronic processor 240 can elect to analyze only a subset of these motions; the presence of certain components of motion in the other motions can be inferred, and appropriate compensation signals, if desired, can be generated automatically. Actuators 230 can be instructed by electronic processor 240 to compensate for angular motion of detector 210, linear motion of detector 210, or a combination of linear and angular motion of detector 210.

Figure 7:
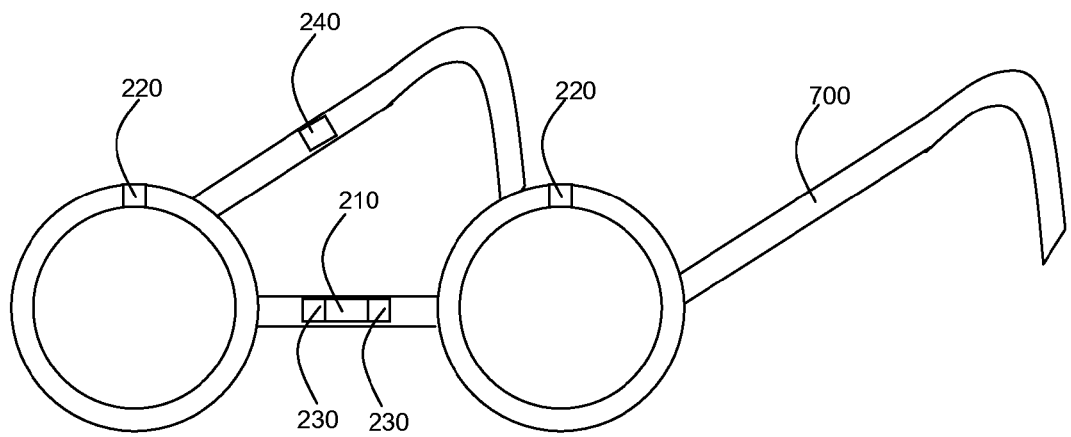
FIG. 7 is a schematic diagram of a vision system integrated within eyeglass frames.

System 200 can be incorporated into a wide variety of housings for purposes of allowing a person with reduced visual acuity to carry the system. In so doing, system 200 enhances the mobility and quality of life of afflicted persons. In some embodiments, system 200 can be enclosed within a housing to form a wearable prosthetic device that functions as disclosed herein. In one such implementation, for example, system 200 is incorporated into eyeglass frames to form a prosthetic device that bears a strong resemblance to an ordinary pair of glasses. FIG. 7 shows such a prosthetic device 700, with a detector 210, sensors 220, actuators 230, and electronic processor 240 embedded into the eyeglass frames. Although the various components of system 200 are embedded in the eyeglass frames in FIG. 7, more generally, some or all of the components can also be attached to the exterior surface of the eyeglass frames as well.

Many other configurations and types of prosthetic devices can also be implemented. While prosthetics configured for head mounting have certain desirable features (e.g., the person wearing the prosthetic can effect a gaze shift by turning his or her head), prosthetic devices can also be worn on other parts of the body and/or carried. When the prosthetic devices include a housing, then as above, some or all of the components can be enclosed within the housing, embedded within the housing, or attached to a surface of the housing.

The disclosure herein describes the use of sensors to detect motion of a detector as visual information is acquired by the detector, and then making adjustments to the position of the detector to compensate for its motion. However, the systems disclosed herein can also be used to compensate detector motion in other ways. For example, in some embodiments, the sensors can be used to detect motion of the detector, and information about the detector's motion can be transmitted to an electronic processor that is configured to process images obtained by the detector. The processor can analyze the images and apply correction algorithms that reduce or eliminate artifacts in the images due to detector motion, using as input the information about detector motion acquired by the sensors. This mode of operation implements a "directed" approach to image processing rather than an iterative approach in which algorithms are not applied iteratively, for example, until one or more threshold conditions related to the "quality" the processed images is achieved. Instead, in a directed approach, the image processing algorithms can estimate the nature of the correction needed, increasing the speed at which corrected images can be produced. Image processing algorithms that can use motion information measured by the sensors disclosed herein to compensate for artifacts in images are disclosed, for example, in the following references, the contents of each of which are incorporated herein by reference in their entirety: J. Chang et al., "Digital image translational and rotational motion stabilization using optical flow technique," IEEE Transactions on Consumer Electronics 48(1): 108-115 (2002); T. Chen, "Video Stabilization Using a Block-Based Parametric Motion Model," Stanford University Dept. of Electrical Engineering Technical Report (2000), available from internet address twiki.cis.rit.edu/twiki/pub/Main/HongqinZhang/chen_report.pdf; A. Censi et al., "Image Stabilization by Features Tracking," IEEE International Conference on Image Analysis and Processing (1999), pp. 665-667; and K. Uomori et al., "Automatic image stabilizing system by full-digital signal processing," IEEE Transactions on Consumer Electronics 36(3): 510-519 (1990).

The preceding discussion has focused, for purposes of clarity of exposition, primarily on using detector 210 to acquire and provide visual information to persons with reduced visual acuity. However, the systems and methods disclosed herein can also be used in many other applications. In general, a wide variety of automated vision systems that are susceptible to undesirable motion of detectors can be compensated as disclosed herein. By detecting motion of the detectors, analyzing the motion to identify different motion components, assigning the components to classes, and then selectively compensating the different components according to class, the effects of undesired motions can be reduced or eliminated while leaving undisturbed the ordinary functions of such systems (e.g., the ability of such systems to intentionally reposition the detectors to control the field of view). Exemplary vision systems to which the methods and systems disclosed herein can be applied include robotic vision systems, manufacturing and assembly line inspection systems, and automated vehicle guidance systems.

Figure 8:
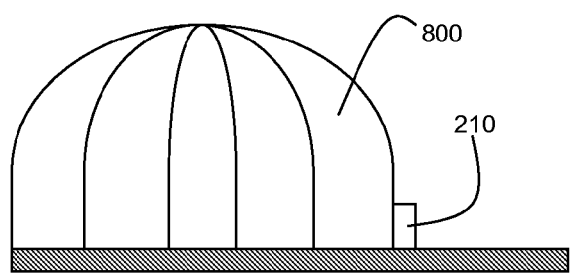
FIG. 8 is a schematic diagram of a hat with a detector for acquiring information that is actively compensated.

In some embodiments, the systems disclosed herein can be integrated into a head covering, such as a hat or cap, or a helmet worn by a soldier, a police officer, an athlete at a sporting event, or another person for whom head protection is important. FIG. 8 shows an embodiment of a hat 800 (e.g., a baseball cap) with a detector 210 mounted to a front surface of the hat. Detector 210 can receive operating power from a power source (not shown in FIG. 8), and can transmit images wirelessly to processor 240, which can also be integrated into hat 800. Although depicted as a baseball cap in FIG. 9, hat 800 can be of a variety of designs. In some embodiments, for example, hat 800 is a protective helmet configured to be worn by a solider, by a fireman, or by another person engaged in hazardous activity and who benefits from receiving the information transmitted by processor 240.

Images (including video signals) captured by detector 210 can be transmitted to a remote receiver 260 (e.g., using a wireless communication interface). The methods disclosed herein can be used to correct for motion of the head-mounted detector so that receiver 260 receives a stabilized video signal for display on a variety of devices including computer screens and televisions. Monitoring of the stabilized video signals allows persons at remote locations to visualize the environment of the person wearing the head covering, permitting persons at remote locations to more accurately perceive situations as they arise and to issue instructions to the wearer, for example.

The systems and methods disclosed herein—in particular, methods for context-dependent analysis and compensation of detectors—can also be applied to measurements of non-visual information. For example, in some embodiments, detector 210 can be configured to measure audio information such as sounds and/or speech (e.g., a microphone). Because audio detectors are generally relatively insensitive to orientation, system 200 may not include sensors 220 or actuators 230. Nonetheless, audio information measured by detector 210 can be transmitted to electronic processor 240. Electronic processor 240 can process the audio information before transmitting it to a wearer or carrier of system 200 (e.g., via an implanted receiver in the wearer/carrier's ear). To process the audio information, electronic processor 240 can be configured to identify different components of the audio information, and to adjust the processing method or output based on the identified components. For example, electronic processor 240 can process the audio information differently if the identified components of the information indicate that the audio information features spoken words recorded in a quiet room, music recorded in a symphony hall, or a mixture of speech and ambient noise in a room with many voices.

In some embodiments, the audio information can be used to control the configuration of the system. The audio information can be processed to identify components, and when certain components are identified, the system is configured (or re-configured) appropriately. For example, when processing of the audio information reveals that an emergency siren is close by on the left-hand side of the wearer of system 200, the orientations of one or more detectors configured to detect visual information can be adjusted so that the detectors so that more visual information is acquired from the direction of the emergency siren. Continued monitoring of the intensity and direction of the emergency siren component of the audio information can be used to allow the visual information detectors to "follow" the siren as it moves, and to discontinue following the siren when it is far away. In this manner described above, system 200 can be configured to make context-sensitive decisions with regard to the processing of measured audio information.

As another example, the systems and methods disclosed herein can be used in sensory substitution devices. Many individuals experience imbalances due to deficiencies in one or more senses. The systems and methods disclosed herein can be used to measure different types of information, to analyze the measured information by identifying different components of the information, and then to process the measured information in a manner that is contextually-dependent on the identified components. The processed information is then conveyed to the individual to assist in compensating for sensory imbalance. Processing of the measured information can depend, for example, on whether the individual is walking, standing, or sitting.

Still further, the systems and methods disclosed herein can be used in sensory augmentation devices (e.g., devices that measure information that is beyond the capability of unaided humans to detect). Such devices can be used to measure, for example, wavelengths of light in the ultraviolet and/or infrared regions of the electromagnetic spectrum, and sounds in frequency bands that are beyond the ordinary range of human hearing. By analyzing this type of information, the systems and methods disclosed herein can associate the information with particular contexts, and tailor processing and delivery of the information to humans accordingly. Context-dependent processing can include, for example, filtering the information to extract portions of interest (e.g., selecting a particular spectral region) within a set of circumstances defined by the context, and discarding irrelevant information.

In some embodiments, the spectral region of interest (e.g., the portion of the spectrum in which subsequent measurements are made) can be changed according to the determined context associated with the initially measured information. For example, if the initially measured information is analyzed and determined to correspond to a context in which high frequency signals are present (e.g., the wearer is engaged in an activity such as whale watching), subsequent measurements of audio information could be made in this high frequency region of the spectrum. The high frequency measured information can then be shifted to a lower frequency region of the spectrum (e.g., within the detection range of the human ear) and presented to the wearer. As another example, if the initially measured information is analyzed and determined to indicate that a fire is (or is possibly) present in the vicinity of the wearer, the system can subsequently measure information about objects in the infrared spectral region. The measured infrared information can be translated into image information in the visible region of the spectrum (so it can be directly observed by the wearer). Alternatively, or in addition, it can be converted into other types of information (such as audio information and/or warnings) which is presented to the wearer. In this manner, the system permits the wearer to perceive information that the wearer would not otherwise detect, augmenting his or her sensory capabilities.

Other Embodiments

A number of embodiments have been described. Nevertheless, it will be understood that various modifications may be made without departing from the spirit and scope of the disclosure. Accordingly, other embodiments are within the scope of the following claims.

What is claimed is:

1. An image stabilization system, comprising:
   a detector configured to detect images;
   an actuator coupled to the detector;
   a sensor coupled to the detector and configured to detect motion of the detector; and
   an electronic processor in communication with the sensor and the actuator, wherein the electronic processor is configured to:
   (a) receive information about motion of the detector from the sensor;
   (b) determine components of the motion of the detector, and associate a class with each of the determined components;
   (c) identify components to be compensated from among the determined components based on the associated classes; and
   (d) generate a control signal that causes the actuator to adjust a position of at least a portion of the detector to compensate for the identified components.

2. The system of claim 1, wherein the sensor comprises at least one of an accelerometer and a gyroscope.

3. The system of claim 1, wherein the detector comprises a camera.

4. The system of claim 1, wherein the motion of the detector comprises at least one of motion along a linear direction and angular motion about an axis.

5. The system of claim 1, wherein the actuator is configured to adjust the position by at least one of translating and rotating the at least a portion of the detector.

6. The system of claim 1, further comprising a support structure to which the detector, actuator, sensor, and electronic processor are attached.

7. The system of claim 6, wherein the support structure comprises eyeglass frames.

8. The system of claim 1, further comprising a receiver in communication with the detector and configured to:
   (a) receive information from the detector, wherein the information is derived from one or more images detected by the detector; and
   (b) transmit a representation of the received information to a human.

9. The system of claim 8, wherein the receiver comprises a visual implant positioned in an eye of the human.

10. The system of claim 1, further comprising at least one additional sensor coupled to the detector, wherein each sensor is configured to detect linear motion along any of three orthogonal axes or angular motion about any one of the three orthogonal axes, and wherein each sensor detects a different motion of the detector.

11. The system of claim 1, wherein the system is worn by a human, wherein one of the associated classes comprises involuntary motion of the detector by the human, and wherein another one of the classes comprises voluntary motion of the detector by the human.

12. A method for image stabilization, the method comprising:
   obtaining image information using a detector;
   detecting motion of the detector while the image information is obtained;
   determining components of the motion of the detector and associating a class with each of the determined components;
   identifying components to be compensated from among the determined components based on the associated classes; and adjusting a position of at least a portion of the detector to compensate for the identified components while the image information is obtained.

13. The method of claim 12, wherein detecting motion of the detector comprises at least one of detecting a linear displacement of the detector along a direction and detecting an angular displacement of the detector about an axis.

14. The method of claim 13, wherein detecting motion of the detector comprises at least one of detecting linear displacements of the detector along at least two orthogonal coordinate directions, and detecting angular displacements of the detector about at least two orthogonal axes.

15. The method of claim 12, wherein one of the classes comprises involuntary motion of the detector by a wearer of the detector, and wherein another one of the classes comprises voluntary motion of the detector by the wearer.

16. The method of claim 12, wherein adjusting the position of at least a portion of the detector to compensate for the identified components comprises directing an actuator coupled to the detector to:
(a) linearly displace the detector along a direction opposite to a linear displacement corresponding to at least one of the identified components; or
(b) angularly displace the detector about an axis in a direction opposite to an angular displacement about the same axis corresponding to at least one of the identified components; or
(c) both (a) and (b).

17. The method of claim 12, wherein determining components of the motion of the detector comprises detecting a magnitude of a displacement of the detector relative to a reference position, and identifying components of the motion based upon the magnitude of the displacement, and wherein the method further comprises associating a class with at least some of the determined components based upon the magnitude of the displacement.

18. The method of claim 12, wherein determining components of the motion of the detector comprises detecting a magnitude of a displacement of the detector relative to a reference position, determining one or more frequencies associated with the displacement of the detector, and identifying components of the motion based upon the one or more frequencies, and wherein the method further comprises associating a class with at least some of the determined components based upon the determined frequencies.

19. The method of claim 12, further comprising transmitting the image information from the detector to a receiver, wherein the detector is worn by a human, and wherein the receiver is a visual implant positioned in an eye of the human.

20. The method of claim 19, further comprising determining a velocity of the detector, and halting transmission of the image information to the receiver when a magnitude of the velocity exceeds a threshold value.

* * * * *